US00PP19051P3

(12) United States Plant Patent
Van Der Knaap

(10) Patent No.: US PP19,051 P3
(45) Date of Patent: Jul. 29, 2008

(54) ***CURCUMA* PLANT NAMED 'CURTINA'**

(50) Latin Name: *Curcuma alismatifolia*
Varietal Denomination: Curtina

(75) Inventor: Leonardus Johannes Maria Van Der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 82 days.

(21) Appl. No.: 11/432,700

(22) Filed: May 11, 2006

(65) Prior Publication Data

US 2007/0266464 P1 Nov. 15, 2007

(51) Int. Cl.
*A01H 5/00* (2006.01)

(52) U.S. Cl. ..... Plt./412
(58) Field of Classification Search ..... Plt./421, Plt./263
See application file for complete search history.

(56) References Cited

PUBLICATIONS

UPOV ROM GTITM Computer Database, GTI Jouve Retrieval Software, Feb. 2007 Citations for 'Curtina'.*

* cited by examiner

*Primary Examiner*—Wendy C. Haas
(74) *Attorney, Agent, or Firm*—Jondle & Associates, P.C.

(57) ABSTRACT

A new *curcuma* plant particularly distinguished by deep-purple flowers with red tips and green leaves with red veins is disclosed.

2 Drawing Sheets

Genus and species: *Curcuma alismatifolia.*
Variety denomination: 'Curtina'.

BACKGROUND OF THE NEW PLANT

The present invention comprises a new and distinct cultivar of *curcuma,* botanically known as *Curcuma alismatifolia,* and hereinafter referred to by the cultivar name 'Curtina'. The new cultivar originated from a hybridization made in May 2001 in De Lier, The Netherlands. The female parent was the proprietary *curcuma* plant '1998248-03' (unpatented), while the male parent was the proprietary *curcuma* plant '1998231-02' (unpatented).

The new cultivar was created in 2001 and has been asexually reproduced repeatedly by in vitro propagation by shoot micropropagation (axillary bud) in Maasdijk, The Netherlands and De Lier, The Netherlands over a two-year period. The present invention has been found to retain its distinctive characteristics through successive asexual propagations.

Plant Breeder's Rights for this cultivar were applied with the European Union on Aug. 10, 2004.

SUMMARY OF THE INVENTION

The following are the most outstanding and distinguishing characteristics of this new cultivar when grown under normal horticultural practices in De Lier, The Netherlands.

1) Deep purple flowers with red tips; and

2) Green leaves with red veins.

DESCRIPTION OF PHOTOGRAPHS

This new *curcuma* plant is illustrated by the accompanying photographs which show the overall plant habit including blooms, buds and foliage of the plant; the colors shown are as true as can be reasonably obtained by conventional photographic procedures. The photographs are of a 140-day old plant grown in a greenhouse in De Lier, The Netherlands.

DESCRIPTION OF THE NEW CULTIVAR

Figure 1:
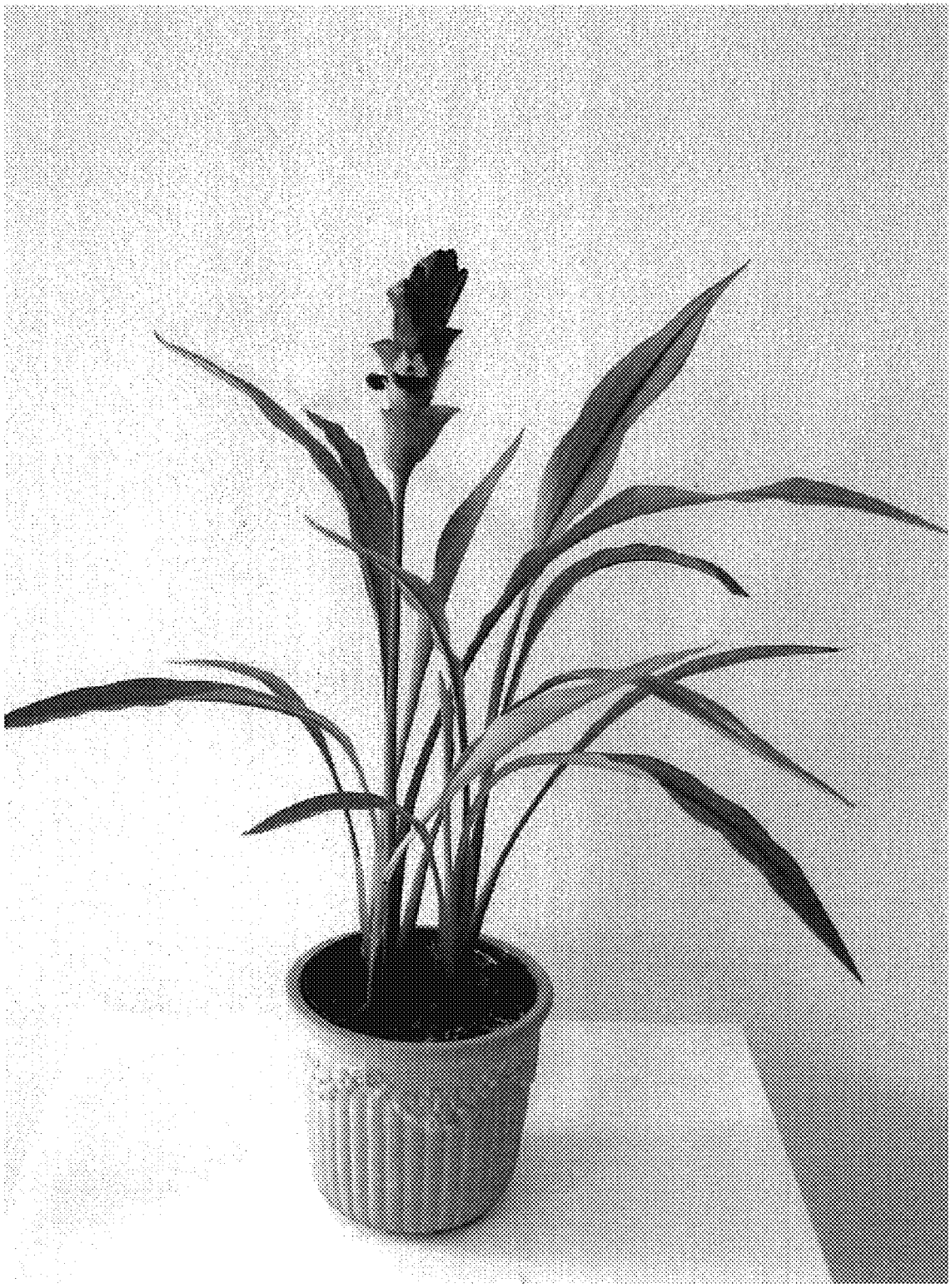
FIG. 1 shows the overall plant habit, including blooms, buds and foliage.
Figure 2:
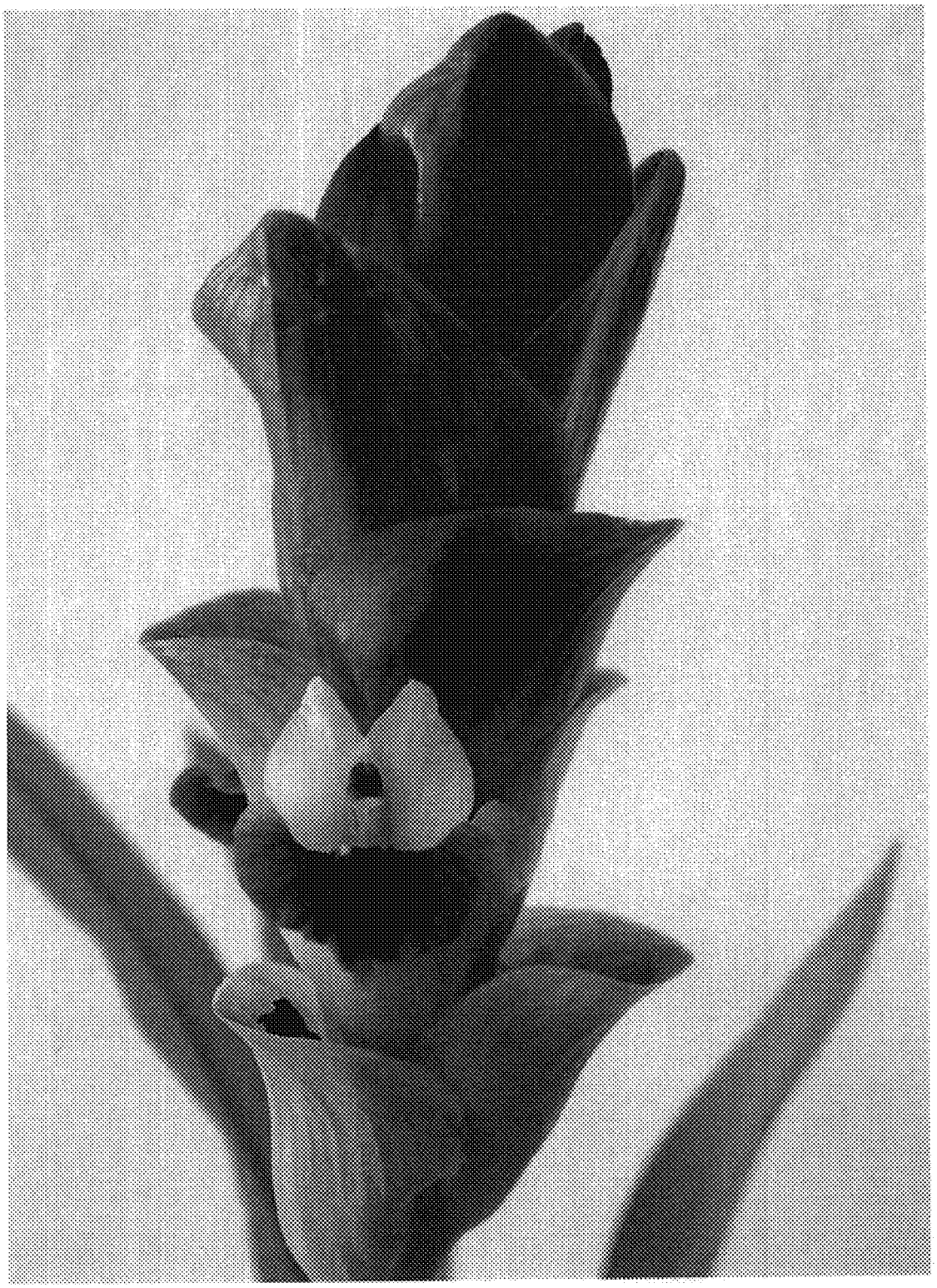
FIG. 2 shows the mature flower.

The following detailed description sets forth the distinctive characteristics of 'Curtina'. The data which define these characteristics were collected from asexual reproductions carried out in De Lier, The Netherlands. The plant history was taken on 140-day old plants which were planted as rooted cuttings in 14-cm pots in 2005 and grown in a glass greenhouse between 19° C. and 28° C. Observations were made in the spring. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Zingiberaceae.
- *Botanical.*—*Curcuma alismatifolia.*
- *Common name.*—Hidden Lily.

Parentage:
- *Female parent.*—'1998248-03', a proprietary dark-pink-flowered *curcuma* plant (unpatented).
- *Male parent.*—'1998231-02', a proprietary purpled-flowered *curcuma* plant (unpatented).

Propagation:
- *Propagation.*—In vitro propagation by shoot micropropagation (axillary bud).
- *Time to initiate and develop roots.*—10 days.
- *Root description.*—RHS 155D, moderately free branching, non-fibrous, slightly fleshy.
- *Average number of rhizomes (per plant).*—6.
- *Rhizome diameter.*—0.5 cm.

Plant:

*Form/growth.*—Rhizotomatous herbaceous perennial, shoots grow from the base.

*Habit.*—Broad, upright with arching leaves.

*Height* (*measured from the soil*).—46.8 cm.

*Width* (*measured from leaf tips*).—42.6 cm.

*Time to produce a finished flowering plant.*—15-weeks for a 10 cm to 15-cm pot.

*Keeping quality.*—28 days.

Leaves:

*Arrangement.*—Alternate.

*Shape.*—Lorate.

*Size.*—Length (fully expanded): 50.0 cm. Width: 3.6 cm.

*Margin.*—Entire.

*Apex.*—Acuminate.

*Base.*—Sheathing, winged; average length of wing is 10.1 cm.

*Aspect.*—Arching.

*Color.*—Upper surface: RHS 137B to RHS 137C. Lower surface: RHS 137B.

*Texture* (*both surfaces*).—Smooth.

*Venation.*—Type: Parallel. Color: Main vein: RHS 166A to RHS 183A. Secondary veins: RHS 137B.

Inflorescence:

*Blooming habit* (*flowering season*).—Spring.

*Lastingness of individual blooms on the plant.*—3 days.

*Fragrance.*—None.

*Inflorescence type.*—Raceme.

*Arrangement.*—Terminal racemes grow from the centers of the shoots.

*Size.*—Length: 13.4 cm. Diameter: 5.9 cm.

Flower description:

*Flowers.*—Size: Length: 2.9 cm. Width: 1.8 cm. Shape: Irregular corolla consisting of three petals, one of which is conspicuous and colorful, flanked by a smaller petal on each side; opposite the large petal is a small labellum consisting of two fused stamen. Color: Upper petal: Upper surface: Darker than RHS 83A while the base is slightly lighter. Lower surface: RHS 83A while the base is lighter. Lateral and lower petals: Upper surface: RHS 85A to RHS 85B while the base is RHS 155B. Lower surface: RHS 85A to RHS 85B while the base is RHS 155B.

*Flower bracts.*—Quantity: 14. Shape: Upper bracts: Broadly ovate. Lower bracts: Reniform to orbicular. Apex: Rounded. Base: Fused. Margin: Entire. Texture: Smooth, glossy. Size: Length: 5.4 cm; the lower bracts are 3.6 cm. Width: 4.1 cm. Color: Upper surface: RHS 71B to RHS 71C; the tip is RHS N79B; the base is slightly tinged with RHS 147C (yellow-green); the lower bracts are RHS 144B with an RHS 183B to RHS 183C (greyed-purple) upper half. Lower surface: RHS 71C to RHS 72A; the tip is RHS N79B; the base is slightly tinged with RHS 147C (yellow-green); the lower bracts are RHS 144A with RHS 183C (greyed-purple) tips.

*Peduncle.*—Color: RHS 137A. Length: 34.6 cm. Diameter: 0.5 cm. Texture: Smooth, rounded, slightly glossy. Angle: Vertical (90°).

Reproductive organs:

*Stamens.*—Quantity: 2, petaloid, fertile. Filament: Length: 1.4 cm. Diameter: 0.4 cm. Color: RHS 85D: tip is darker, RHS 86A. Anther color: RHS 155D. Pollen: Absent.

*Pistil.*—Quantity: 1. Length: 2.0 cm.

*Style.*—Length: 1.9 cm. Diameter: 0.05 cm. Color: RHS N155A.

*Stigma.*—Length: 0.1 cm. Diameter: 0.15 cm. Color: RHS N155A.

Fruit and seed set: Seed production has not been observed to date.

Disease and insect resistance: No particular resistance or susceptibility to diseases or insects noted to date. Similar to other *curcuma* varieties.

COMPARISON WITH PARENTAL AND COMMERCIAL CULTIVARS

'Curtina' differs from the female parent '1998248-03' (unpatented), by having deep-purple flowers with red tips, while '1998248-03' has dark-pink flowers with green tips.

'Curtina' differs from the male parent '1998231-02' (unpatented), by having deep-purple flowers and green leaves with red veins, while '1998231-02' has purple flowers and green leaves with no veins.

'Curtina' differs from the commercial variety 'Curleno' (unpatented), by having deep-purple flowers and green leaves with red veins, while 'Curleno' has pink-white flowers and green leaves with no veins. In addition, 'Curtina' has a long flower stem, while 'Curleno' has a medium flower stem.

I claim:

1. A new and distinct cultivar of *curcuma* plant as shown and described herein.

* * * * *